United States Patent [19]

Maytal

[11] Patent Number: 5,577,387
[45] Date of Patent: Nov. 26, 1996

[54] CONTROLLED CRYOGENIC CONTACT SYSTEM

[75] Inventor: Ben-Zion Maytal, Atlit, Israel

[73] Assignee: State of Israel, Ministry of Defence, Rafael-Armaments Development Authority, Israel

[21] Appl. No.: 600,462

[22] Filed: Feb. 13, 1996

Related U.S. Application Data

[62] Division of Ser. No. 195,555, Feb. 14, 1994.

[30] Foreign Application Priority Data

Nov. 1, 1993 [IL] Israel .......................................... 107460

[51] Int. Cl.⁶ ..................................................... F25B 19/00
[52] U.S. Cl. .................. 62/51.2; 62/62; 62/293
[58] Field of Search ................................ 62/62, 293, 51.2

[56] References Cited

U.S. PATENT DOCUMENTS

| | | |
|---|---|---|
| 3,388,128 | 6/1968 | Day et al. . |
| 3,398,738 | 8/1968 | Lamb et al. . |
| 3,477,434 | 11/1969 | Hood, Jr. et al. . |
| 3,696,813 | 10/1972 | Wallach . |
| 3,782,386 | 1/1974 | Barger et al. . |
| 3,823,575 | 7/1974 | Parel . |
| 3,924,628 | 12/1975 | Droegemueller et al. . |
| 3,993,075 | 11/1976 | Lisenbee et al. . |
| 4,126,017 | 11/1978 | Bytniewski et al. . |
| 4,587,959 | 5/1986 | Ruderian . |
| 4,946,460 | 8/1990 | Merry et al. . |
| 5,139,496 | 8/1992 | Hed . |
| 5,147,355 | 9/1992 | Friedman et al. . |
| 5,365,750 | 11/1994 | Greenthal . |

FOREIGN PATENT DOCUMENTS

| | | |
|---|---|---|
| 0380217 | 8/1990 | European Pat. Off. . |
| 0447861 | 9/1991 | European Pat. Off. . |
| 0608927 | 8/1994 | European Pat. Off. . |
| 2207730 | 6/1974 | France . |
| 2242062 | 3/1975 | France . |
| 2368264 | 5/1978 | France . |
| 2399828 | 3/1979 | France . |
| 2477406 | 9/1981 | France . |
| 2482445 | 11/1981 | France . |
| 2638206 | 3/1977 | Germany . |
| 3343664 | 3/1985 | Germany . |
| 3716746 | 12/1988 | Germany . |
| 0774549 | 10/1980 | U.S.S.R. . |
| 1217377 | 3/1986 | U.S.S.R. . |
| 1422445 | 1/1976 | United Kingdom . |
| 90/08144 | 7/1990 | WIPO . |
| 93/08752 | 5/1993 | WIPO . |
| 93/18714 | 9/1993 | WIPO . |

OTHER PUBLICATIONS

Andrew A. Gage, "Current Issues in Cryosurgery", *Cryobiology*, vol. 19, 1982, pp. 219–222.

*Primary Examiner*—Ronald C. Capossela
*Attorney, Agent, or Firm*—Merchant, Gould, Smith, Edell, Welter & Schmidt

[57] ABSTRACT

An apparatus for creating controlled temperature changes on a contact surface, comprises: a) a probe having a contact surface, which probe is suitable for creating fast temperature changes at the said contact surface; b) temperature generation means, coupled to the said probe, being capable of creating cryogenic and above 0° C. temperatures at the said contact surface of the said probe; and c) processing means to control the said temperature generation means according to predetermined operating conditions.

2 Claims, 5 Drawing Sheets

CONTROLLED CRYOGENIC CONTACT SYSTEM

This is a Divisional application of application Ser. No. 08/195,555, filed Feb. 14, 1994, which application(s) are incorporated herein by reference.

FIELD OF THE INVENTION

The present invention relates to apparatus for carrying out operations involving cryogenic temperatures as well as temperatures above 0° C. More particularly, the invention is directed to apparatus which permits to carry out such operations in a highly controlled manner.

BACKGROUND OF THE INVENTION

The ability to cause fist changes in temperatures, particularly between very low temperatures and room or higher temperatures, on a desired surface and at a desired location, is of practical importance in many uses. Fast temperature changes can be exploited, for instance, in the treatment of various materials, for sealing or surface curing purposes, etc.

Cold and hot surfaces are used also for medical uses. For instance, cryogenic techniques are employed to destroy malignant tissues, or plastic surgery. One example of such a use is presented in SU 774,549, which relates to a thermal treatment of biological tissues by passing heat earners through a cryosurgical probe. The method is said to be useful in the cryo-surgery of the human brain. This method, however, involves passing a heat carrier through a surgical probe, its subsequent heating and repeated passage through the probe. Acetone or alcohol are used as the heat carrier. Prior to its passage through the probe the heat carrier is either cooled to –70°–75° C., or heated to +70°–90° C.

Devices of this type present severe drawbacks, inasmuch as they have long lags in temperature changes, they require cumbersome heating/cooling apparatus outside the probe, and are complicated and expensive to use.

Cryosurgical instruments having both cryocooling and heating capabilities are also known in the art. One such device and its medical use have been described by Andrew A. Gage ["Current Issues in Cryosurgery", *Cryobiology* 19, 219–222(1982), at pp. 220–21]. The device described therein was cooled by liquid nitrogen and electrically heated, to provide hemostasis. The electrical heating, however, by its nature is a relatively slow procedure.

Another device is described in SU 1,217,377, which exploits the expansion of gases through an orifice. However, simple expansion of gas through an orifice provides relatively slow temperature changes, and the changes in temperature are relatively mild. Thus, for instance, in the device of SU 1,217,377 it is not possible to liquefy nitrogen. Additionally, this prior art device employs helium at room temperature which, expanding from a pressure of about 300 atmospheres, will attain a heating of merely about 30° C. In any case, in the single pass expansion described in this reference, liquefaction of nitrogen cannot be achieved. However, helium has an inversion temperature of about 45K, which renders it possible to employ neon or hydrogen as the second gas, as is done in this reference. The highest inversion temperature of neon is about 200K, and of hydrogen is about 180K. Accordingly, these gases cannot be used while using nitrogen as the first gas, because the temperature of liquid nitrogen is 80K, and thus the heating obtainable with neon and hydrogen is low. Additionally, neon and hydrogen may be found at an inversion temperature lower than their maximal temperature, so that no heating is obtained. However, neon is expensive and hydrogen is dangerous, and the obtainable temperatures are unsatisfactory for many uses, which accounts for the lack of success of the above-mentioned device.

Copending Israeli Patent Application No. 104506, filed Jan. 25, 1993 by the same applicant hereof, the specification of which is incorporated herein by reference, provides a method by means of which a fast and periodic change of surface temperature, even down to cryogenic range, can be created, at the desired location, in a simple and effective manner. This is achieved by creating a surface having a fast changing temperature, by providing a heat exchanger coupled to an orifice opening into a jacket which is in contact with the surface to be heated and cooled, the said jacket forming a reservoir capable of housing a fluid in contact with the surface to be heated and cooled, and providing two gas sources, each gas source being independently connected to the said heat exchanger, one source providing a first gas, which liquefies when it expands through the said orifice, and the other gas source providing a second gas, having an inversion temperature lower than the temperature obtained by the liquefaction of the first gas, and causing the exhaust gas flowing out from the said jacket, to flow through the said heat-exchanger to preheat or precool the inflowing gas, as the case may be, and further causing the said first and the said second gas alternately to flow through the said heat exchanger and orifice, to cool or to heat the said surface; means being provided for allowing and stopping the flow of each gas through the said orifice.

The selection of appropriate gases is crucial. For instance, the maximum inversion temperature of helium is 43K. Thus, even when somewhat precooled by boiling nitrogen at 77.3K, it still will warm up when undergoing Joule-Thomson expansion. Furthermore, providing a preheating or precooling of the inflowing gas is not just a matter of efficiency or saving, but is an essential part of the invention, since processes and devices employing a one-pass heating or cooling, without utilizing an exchange of heat via an appropriate heat-exchanger, will not provide sufficiently low or sufficiently high temperatures, and will result in a temperature change which is excessively slow.

Heat exchangers can be of any type, and may be, e.g., a finned tube heat-exchanger of a porous-matrix heat-exchanger, e.g., of the type described in British Patent No. 1,422,445. The device described in this British patent provides only for the cryocooling of the probe, the purpose being to maintain the temperature of the probe below –80° C., thus avoiding altogether the need for heating the probe. It should be mentioned that, according to the teachings of this patent, heating was necessary, when operating at temperatures above –80° C., for the purpose to prevent the probe from sticking to the tissue. However, when operating according to IL 104506, with fast cooling-heating cycles, the heat exchanger can be utilized also for heating purposes.

The first gas is preferably selected from the group consisting essentially of argon, nitrogen, air, krypton, $CF_4$, xenon and $N_2O$, and the second gas is helium.

Cryogenic liquefaction occurs at the tip of the cold extremity of the device operating according to IL 104506, under the cooled metal surface. The Linde-Hampson method is applied, using the Joule-Thomson effect, for cooldown to liquefaction.

IL 104506 also describes an apparatus for the cryocooling and the heating of surfaces, comprising:

1) a heat exchanger coupled to an orifice, the said orifice opening into a jacket;
2) a jacket which is in contact with the surface to be heated and cooled, the said jacket forming a reservoir capable of housing a fluid in contact with the surface to be heated and cooled:
3) two pressurized gas sources, each gas source being independently connected to the said heat exchanger;
4) means for allowing and stopping the flow of each gas through the said orifice.

The method of IL 104506 makes it possible to obtain a high frequency of temperature change. Thus, for instance, one may which, for a given application, to oscillate between temperatures of −50° C. and +100° C. only.

SUMMARY OF THE INVENTION

It has now been found, and this is an object of the present invention, that it is highly advantageous to be able to control the operation of the heating/cooling device the temperature of which changes rapidly, for a variety of uses and applications.

It is an object of the present invention to provide an apparatus which permits to control the temperature obtained on the contact surface of a probe in which heating and cooling is achieved by the Joule-Thomson effect obtained through the expansion of gases.

It is another object, of the invention to provide an apparatus which can be easily operated by unskilled operators while providing highly precise and controlled temperatures.

It is still another object of the invention to provide an apparatus which can be pre-programmed to create desired temperature changes with time in an appropriate probe.

It is still a further object of the invention to provide a relatively inexpensive, easy to use and convenient to operate apparatus of the type described above. Other objects of the invention will become apparent as the description proceeds.

The apparatus for creating controlled temperature changes on a contact. surface, according to the invention, comprises:
  a) a probe having a contact surface, which probe is suitable for creating fast temperature changes at the said contact surface;
  b) temperature generation means, coupled to the said probe, being capable of creating cryogenic and above 0° C. temperatures at, the said contact surface of the said probe; and
  c) processing means to control the said temperature generation means according to predetermined operating conditions.

The temperature generation means can be of any suitable type, including but not limited to gas expansion, electric means, and their combinations. According to a preferred embodiment of the invention the apparatus comprises:
  a) a probe comprising:
    1) heat exchanging means coupled to an orifice, the said orifice opening into a jacket;
    2) a jacket which is in contact with the surface to be heated and cooled, the said jacket forming a reservoir capable of housing a fluid in contact with the surface to be heated and cooled;
    3) two independent connections for pressurized gas sources, connected to the said heat exchanger;
  b) two independent pressurized gas sources, connected to the said probe through the said two independent connections;
  c) controllable gas flow valves to permit or preclude the flow of each of the gases from the said independent pressurized gas sources into the said probe;
  d) processing means to control the said controllable gas flow rate valves according to predetermined operating conditions.

The probe can be any suitable probe, of any type and shape, which utilizes the Joule-Thomson effect. For example, the probe described in IL 104506 can be suitably used for this purpose.

According to a preferred embodiment of the invention, the apparatus comprises external data input means, to provide operation data to the processing means, such as a keyboard, a communication port, e.g., RS232, or magnetic or optical reading means, to read pre-prepared data.

The apparatus may further comprose display means to display data written to, or read from, the processing means. The processing means can be of any suitable type, e.g., the apparatus may be coupled to a microcomputer programmed to carry out the functions described herein, as well as any other desired auxiliary function.

According to a preferred embodiment of the invention, the apparatus further comprises temperature-reading means located at or near the contact surface, which temperature-reading means provide temperature readings to the processing means. Such temperature-reading means may comprise, e.g., one or more thermocouples, but at least two thermocouples are preferred, to ensure continued feedback temperature readings. The temperature readings permit the processing means to determine whether the temperature is to be increased or decreased, in order to remain at the predetermined temperature, and to close or open the appropriate valves.

A further advantage of the apparatus of the invention is that it permits to alert the operator, when using pressurized gas reservoirs, of the remaining lifetime of the gas reservoir. In order to do so, in a preferred embodiment of the invention there are provided pressure-reading means located between the pressurized gas source and the probe, to provide to the processing means readings corresponding to pressure supplied by each pressurized gas source. Thus, during the emptying of a gas reservoir, its pressure decreases and the processing means, which keeps track of such pressures, can calculate the expected operation time remaining with the reservoir, on the basis of pressure changes with time in the specific operation undertaken.

The invention is also directed to a method of creating controlled temperature changes on a contact surface, comprising:
  a) providing a probe having a contact surface, which probe is suitable for creating fast temperature changes at the said contact surface;
  b) providing temperature generation means, coupled to the said probe, the said temperature generation means being capable of creating positive and negative temperatures at the said contact surface of the said probe;
  c) connecting processing means to the said probe and to the said temperature generating means:
  d) providing to the said processing means desired temperature values and/or profiles; and
  e) controlling the temperature of the contact surface of the probe to obtain the said desired temperature values and/or profiles by controlling, by means of the said processing means, the activity of the said negative and of the said positive temperatures generating means.

According to a preferred embodiment of the invention the method comprises:

a) providing a probe comprising:
   1) heat exchanging means coupled to an orifice, the said orifice opening into a jacket;
   2) a jacket which is in contact with the surface to be heated and cooled, the said jacket forming a reservoir capable of housing a fluid in contact with the surface to be heated and cooled;
   3) two independent connections for pressurized gas sources, connected to the said heat exchanger;
b) providing two independent pressurized gas sources, connected to the said probe through the said two independent connections;
c) providing controllable gas flow valves to permit or preclude the flow of each of the gases from the said independent pressurized gas sources into the said probe:
d) providing processing means and programming them to control the said controllable gas flow rate valves according to predetermined operating conditions.

All the above and other characteristics and advantages of the invention will be better understood through the following illustrative and non-limitative description of preferred embodiment.

DETAILED DESCRIPTION OF PREFERRED EMBODIMENTS

Figure 1:
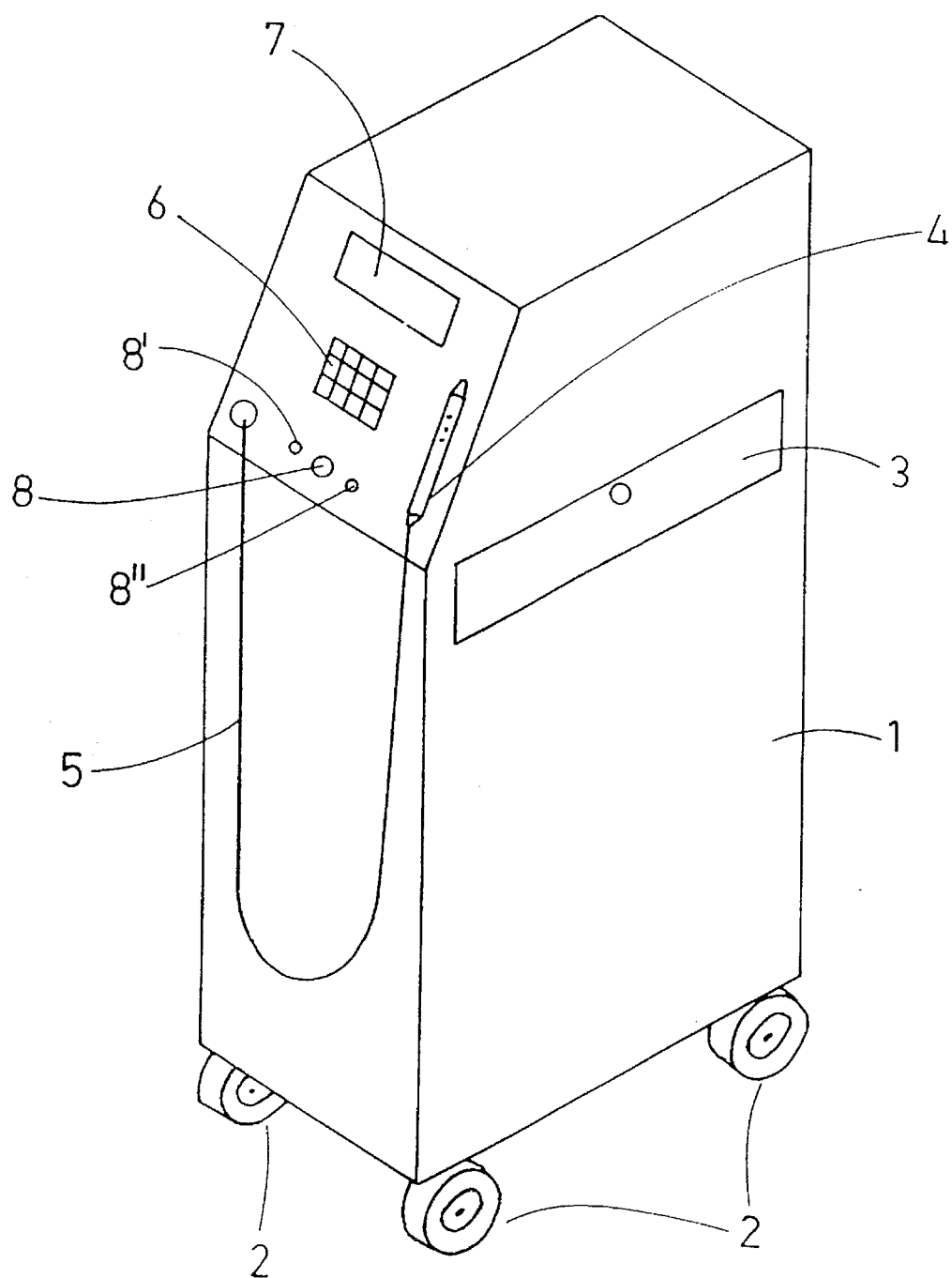
FIG. 1 is a schematic perspective view of an apparatus according to one preferred embodiment of the invention.

FIG. 1 illustrates a device according to a preferred embodiment of the invention. This device is designed to be movable and self-supporting, and does not require connection to outside gas sources. It, consists of a body 1, provided with wheels 2, which houses two gas reservoirs (not, shown). The reservoirs can be replaced through the backdoor, which is not seen in the figure. An addition door 3 gives access to the inside of the body, and is used for parts replacement and maintenance, as well as for housing spare parts.

A probe 4 is connected to the gas reservoirs and to a microprocessor, as explained above and in further detail below, through line 5. All connections are within body 1. A keyboard 6 and a display 7 are provided on the front panel of the apparatus, along with on-off switch 8 control lights 8' and 8", which can be used to indicate the operation status of the apparatus, e.g., to indicate at any given time whether it is cooling or heating.

Since the electric power requirements of the apparatus are relatively very low, the apparatus is powered by a DC source, such as a battery, but may alternatively be connected to an AC source.

Figure 2:
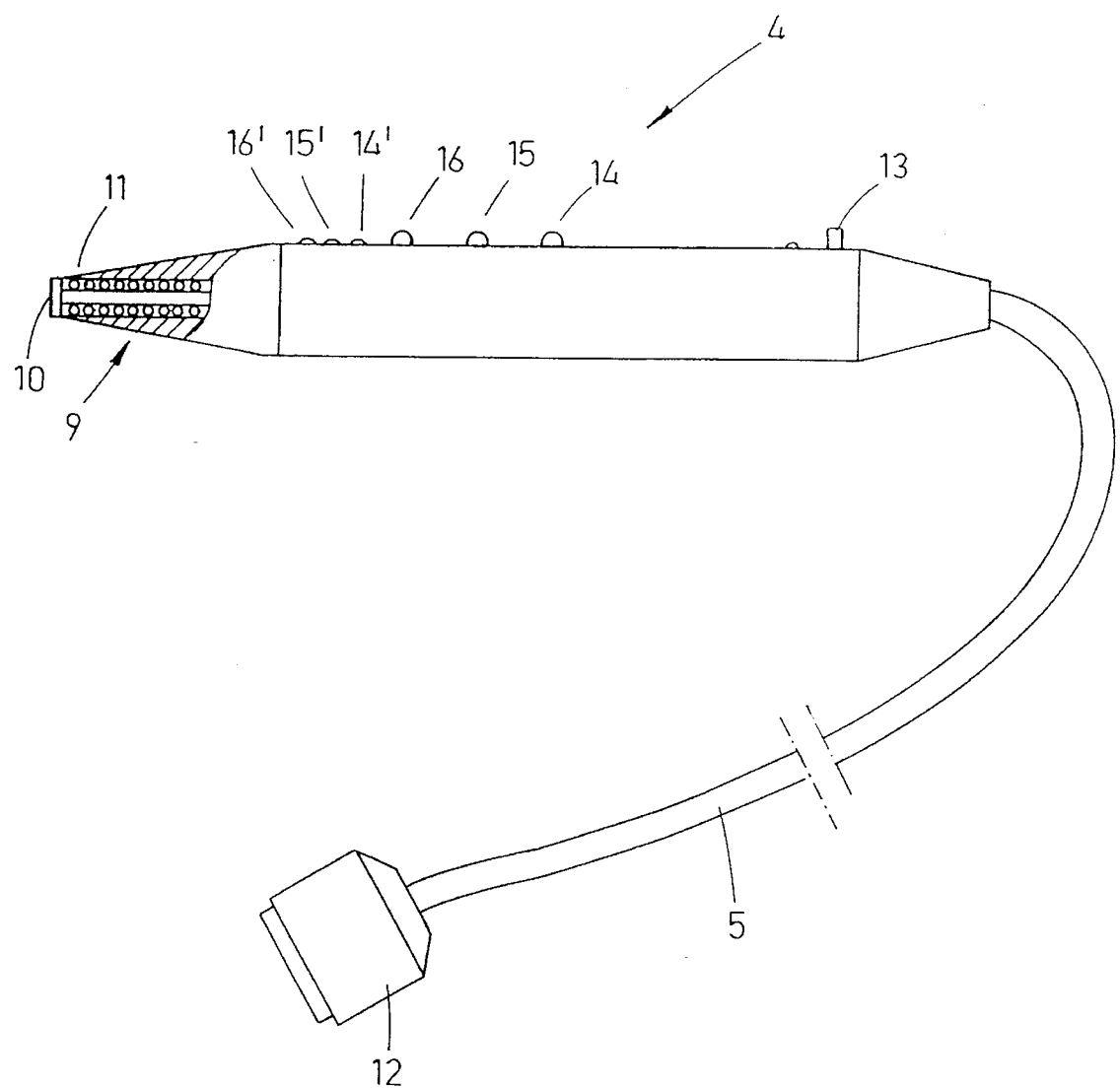
FIG. 2 schematically shows of a probe, according to one preferred embodiment of the invention, shown in partial cross-section.

FIG. 2 shows the probe 4 of FIG. 1 in greater detail. The Joule-Thomson heat exchanger 9 serves contact surface 10, which is heated or cooled, depending on the nature of the gas flowing therethrough. Thermocouple 11 is in close contact with the inner part of contact surface 10, and detects the temperature at that location. The thermocouple wire is led to the processing means through line 5 and connector 12 leaving the probe is exhausted to the atmosphere either through connections in the probe, or at connector 12.

The probe is provided with a main switch 13, operating switches 14, 15 and 16, and monitor lights 14', 15' and 16'. These switches operate the probe towards cooling or heating, or for preset cooling/heating cycles, and the lights indicate the operation being performed. Manual operation or microprocessor-controlled operation can be chosen.

Figure 3:
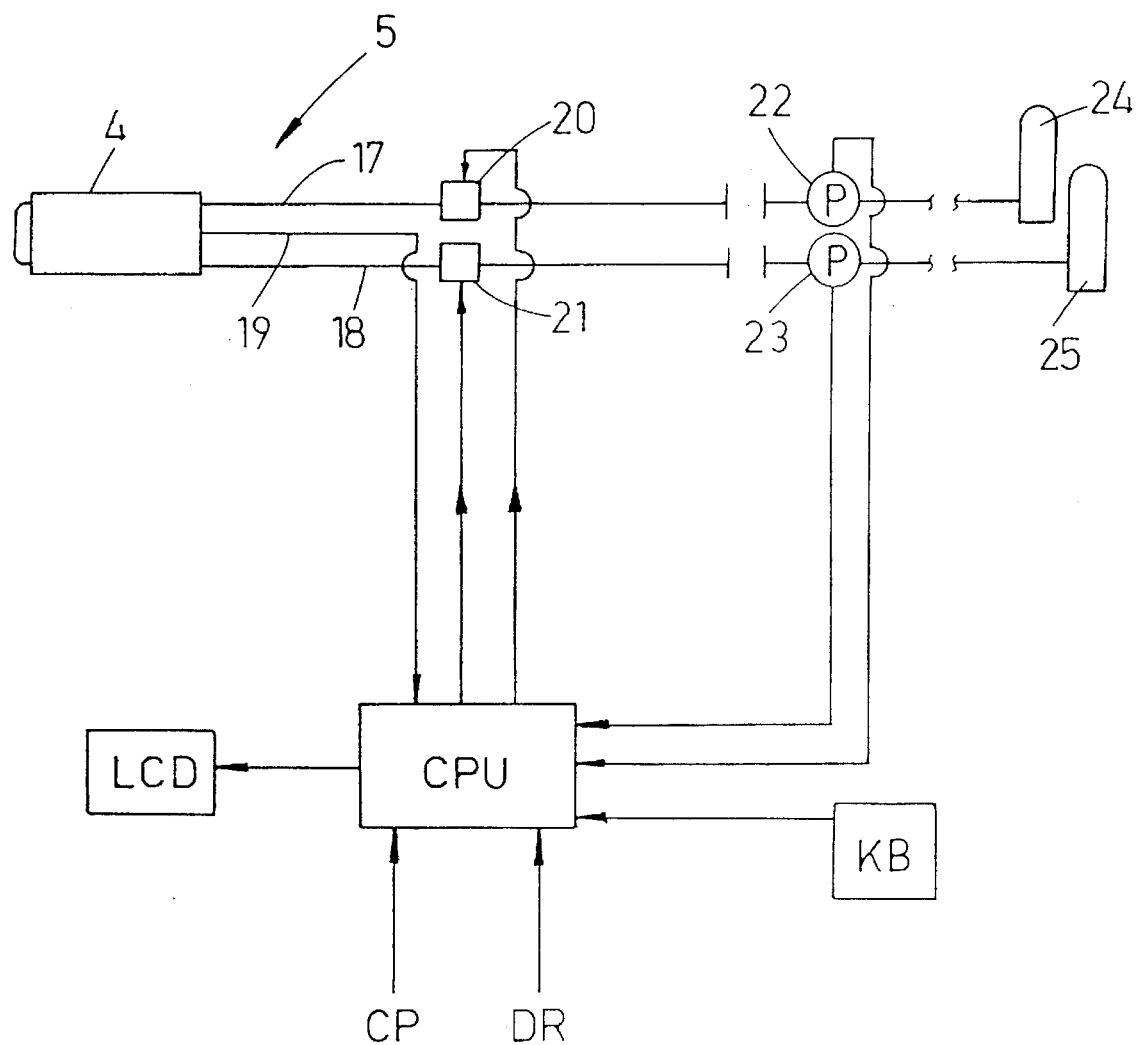
FIG. 3 schematically illustrates the controlled operation of the apparatus of FIG. 1.

Looking now at FIG. 3, a central processing unit (CPU) controls the operation of the apparatus, according to predetermined operating conditions provided to it. Programming of the operating conditions can be made through keyboard 6 of FIG. 1 (indicated by KB in the figure), or through a communication port CP, connected to a programming computer, or through a data reader DR, e.g., a magnetic or optical reader. The data can be displayed on a display, e.g., a liquid crystal display (LCD), and the keyboard can be used also to read data from the CPU and to display them on the LCD. The CPU can be provided with a substantial memory, so as to store not only operating parameters to be controlled, but also data received during the operation, e.g., temperature or pressure readings.

Data contained in the memory of the CPU can be print out, e.g., through an RS232 or similar port.

Line 5 of probe 4 contains two incoming gas lines, 17 and 18, as well as an outgoing thermocouple line 19, the readings of which are fed to the CPU. In response, and in order to maintain the preprogrammed temperature in the probe contact surface, the CPU operates the two controllable valves 20 and 21, which control the flow of gas into the probe 4. Two pressure gauges, 22 and 23, provide pressure readings to the CPU, which relate to the pressure in reservoirs 24 and 25.

EXAMPLE 1

An apparatus was built according to the embodiment described above. It included E-type thermocouples, a 18 mm diameter probe, with a length of 160 mm. The gases employed where argon (for cooling) and helium (for heating). The diameter of the contact surface of the probe was 6 mm.

Figure 4:
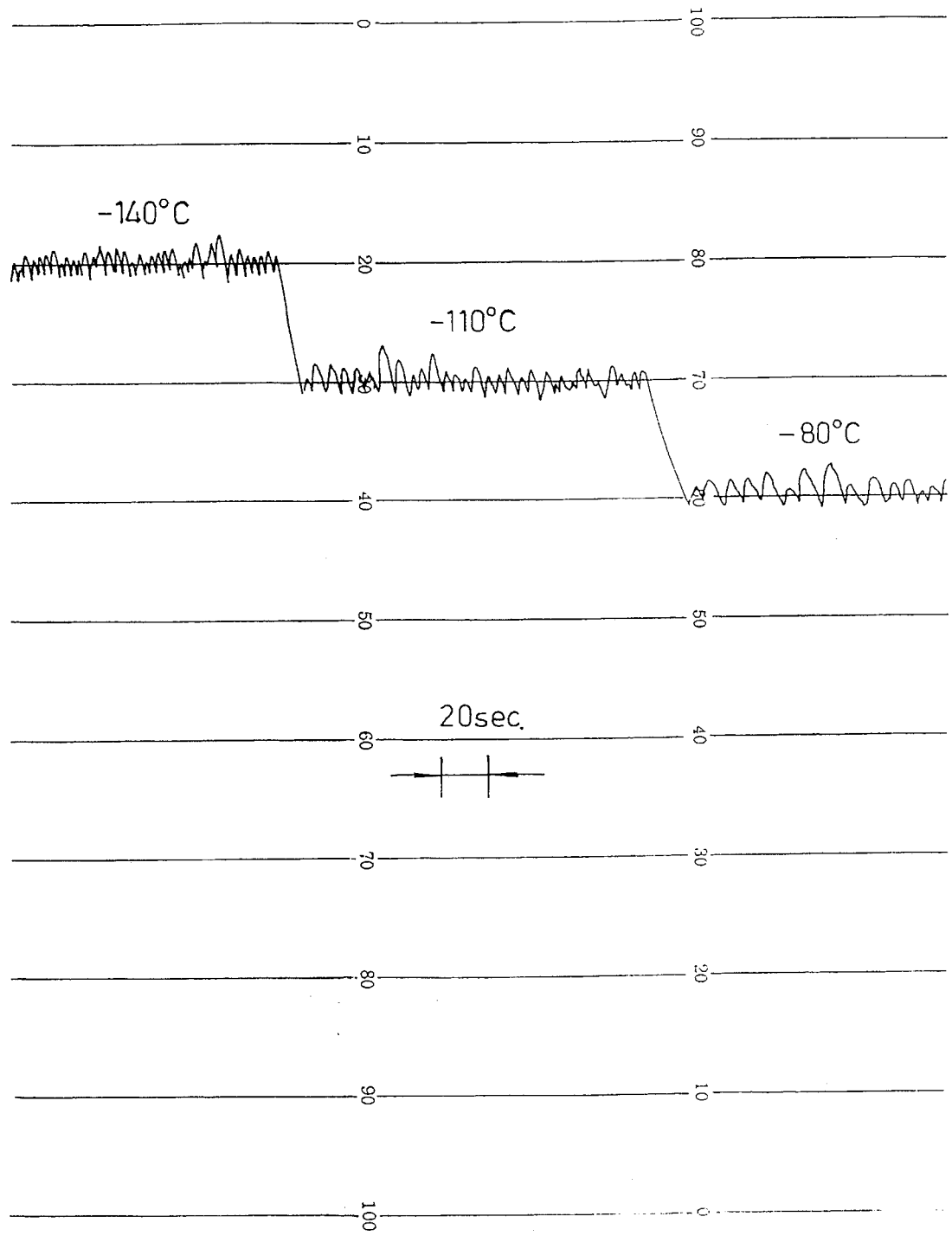
FIG. 4 shows controlled temperature readings taken at the contact surface of the probe of FIG. 2, coupled to the apparatus of FIGS. 1 and 3, in the experiment described in Example 1.

In order to test the controllability of the apparatus, the temperatures range was set around a single temperature at a given time, and three different temperatures were tested, these were −140° C., −120° C. and −80° C. Each temperature was maintained for 5 minutes, as seen in FIG. 4 which shows the thermocouple readings (11 in FIG. 2) for this experiment. It can be seen that the apparatus of the invention is capable of maintaining a virtually constant temperature, by alternating two different gases with a high frequency.

EXAMPLE 2

The apparatus of Example 1 was used in an experiment in which it was desired periodically to cool a surface to cryogenic temperature (−165° C.) and then to above-zero temperature (44° C.), the frequency of oscillation between the two extreme temperatures being required to be 38 seconds. These data were fed to the CPU, which was preprogrammed accordingly. The details of the computer program are not given herein for the sake of brevity, since providing an appropriate program is within the scope of the routineer.

Figure 5:
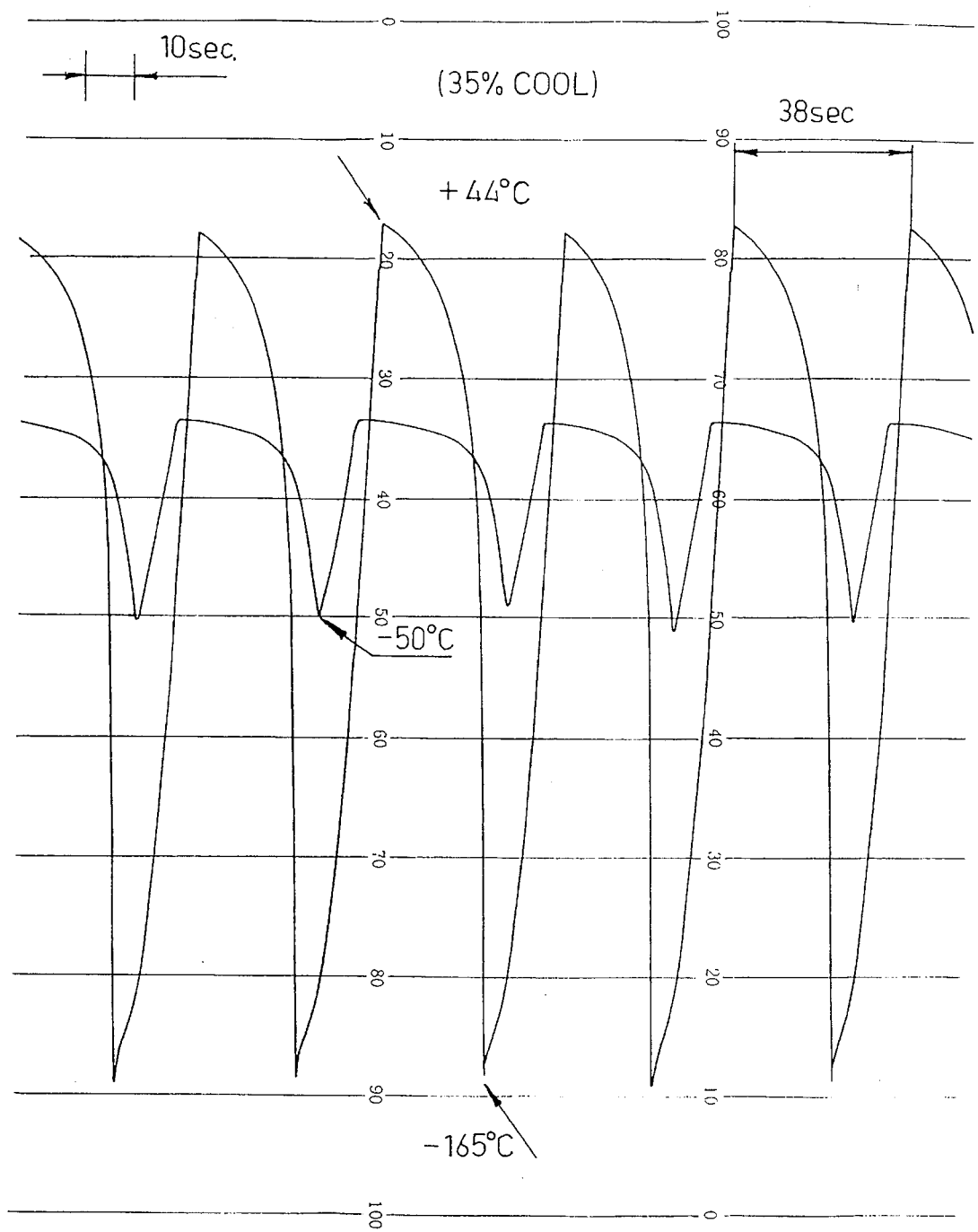
FIG. 5 shows controlled temperature readings taken under the contact surface of a speciment, in the experiment described in Example 2.

The specimen on the surface of which the probe was applied was a potato. The resulting temperature readings at the contact surface are shown in FIG. 5. Additional temperature readings were taken within the potato, at a depth of 2 mm below its surface, directly below the contact surface of the probe. The resulting temperature cycles within the potato are also depicted in FIG. 5 (smaller wave), and it can be seen that the minimal temperature reached at a depth of 2 mm is about −50° C., using a probe temperature of −165° C. The highest temperature at the same depth was about 0° C. As indicated on the figure, about 35% of the 38 seconds cycle was devoted to cooling, and 65% to heating.

All the above description and examples have been provided for the purpose of illustration, and are not intended to limit the invention in any way. Many modifications can be effected in the various parts, shape and construction of the apparatus of the invention, different and additional functions can be performed by the apparatus described above, all without exceeding the scope of the invention.

I claim:

1. A method of creating controlled temperature changes on a contact surface, comprising:
   a) providing a probe having a contact surface, which probe is suitable for creating fast temperature changes at the said contact, surface;
   b) providing temperature generation means, coupled to the said probe, the said temperature generation means being capable of creating positive and negative temperatures at the said contact surface of the said probe;
   c) connecting processing means to the said probe and to the stud temperature generating means;
   d) providing to the said processing means desired temperature values and/or profiles; and
   e) controlling the temperature of the contact surface of the probe to obtain the said desired temperature values and/or profiles by controlling, by means of the said processing means, the activity of the said negative and of the said positive temperatures generating means.

2. A method according to claim 1, comprising:
   a) providing a probe comprising:
      1) heat exchanging means coupled to an orifice, the said orifice opening into a jacket;
      2) a jacket which is in contact with the surface to be heated and cooled, the said jacket forming a reservoir capable of housing a fluid in contact with the surface to be heated and cooled;
      3) two independent connections for pressurized gas sources, connected to the said heat exchanger;
   b) providing two independent pressurized gas sources, connected to the said probe through the said two independent connections;
   c) providing controllable gas flow valves to permit or preclude the flow of each of the gases from the said independent pressurized gas sources into the said probe;
   d) providing processing means and programming them to control the said controllable gas flow rate valves according to predetermined operating conditions.

* * * * *

UNITED STATES PATENT AND TRADEMARK OFFICE
CERTIFICATE OF CORRECTION

PATENT NO. : 5,577,387

DATED : November 26, 1996

INVENTOR(S) : Ben-Zion Maytal

It is certified that error appears in the above-identified patent and that said Letters Patent is hereby corrected as shown below:

Col. 1, line 26: insert --for-- before the word "plastic"

Col. 1, line 28: delete "earners" and replace with --carriers--

Col. 4, line 15: "cornprose" should read --comprise--

Col. 5, line 54: "addition" should read --additional--

Col. 8, line 4, claim 1: "stud" should read --said--

Signed and Sealed this

Twenty-first Day of October 1997

Attest:

BRUCE LEHMAN

Attesting Officer

Commissioner of Patents and Trademarks